United States Patent [19]

Darsow

[11] Patent Number: 5,770,744
[45] Date of Patent: *Jun. 23, 1998

[54] PROCESS FOR THE PREPARATION OF SUCCINIC ANHYDRIDE

[75] Inventor: Gerhard Darsow, Krefeld, Germany

[73] Assignee: Bayer Aktiengesellschaft, Leverkusen, Germany

[ * ] Notice: The term of this patent shall not extend beyond the expiration date of Pat. No. 5,606,099.

[21] Appl. No.: 584,866

[22] Filed: Jan. 11, 1996

[30] Foreign Application Priority Data

Jan. 20, 1995 [DE] Germany .................. 195 01 676.9

[51] Int. Cl.⁶ .......................... C07D 307/60; C07C 5/00; C08F 24/00

[52] U.S. Cl. ................... 549/233; 585/250; 526/270; 526/908; 526/915

[58] Field of Search .................. 549/233; 585/250; 526/915, 908, 270

[56] References Cited

U.S. PATENT DOCUMENTS

| 2,198,153 | 4/1940 | Coons | 260/341 |
|---|---|---|---|
| 5,606,099 | 2/1997 | Darsow | 560/190 |

FOREIGN PATENT DOCUMENTS 1226556  10/1966  Germany .

OTHER PUBLICATIONS

Ma, "Process for Making Succinic Anhydride . . . " CA, vol. 121 (1994), p. 8685.
Ullman Encyclopedia of Industrial Chemistry, 3rd ed., vol. 4, p. 318, (1953).
Chemical Abstracts, vol. 34, Abstract No. 4521, abstract of G.B. 567,952, (1939).
Chemical Abstracts, Abstract No. 54659, abstract of U.S. 2,198,153 (1940).
Chemical Abstracts, vol. 61, pp. 8195 & 285.
Chemical Abstracts, vol. 93, Abstract No. 93:71047b, p. 912, abstract of USSR 721,406, (1980).
Chemical Abstracts, vol. 79, Abstract No. 5013x, p. 425, abstract of JP 73–07,609 (1973).

*Primary Examiner*—Mukund J. Shah
*Assistant Examiner*—Tamthom T. Ngo
*Attorney, Agent, or Firm*—Sprung Kramer Schaefer & Briscoe

[57] ABSTRACT

Maleic anhydride can be hydrogenated with hydrogen to give succinic anhydride by a catalyzed liquid-phase hydrogenation, by carrying out the hydrogenation continuously at a pressure of 50 to 400 bar and a reaction temperature of 60° to 180° C. on oxygen-free and support-free shaped bodies arranged in the fixed bed, which shaped bodies are made of pressed powders of the elements of the iron subgroup of subgroup VIII of the Periodic Table of the Elements or of their alloys with each other or of their alloys with elements of subgroup VI; in addition, hydrogenation-inert elements can be present. The shaped bodies have a compressive strength of 20 to 250N and an internal surface area of 10 to 90 $m^2/g$.

15 Claims, No Drawings

PROCESS FOR THE PREPARATION OF SUCCINIC ANHYDRIDE

BACKGROUND OF THE INVENTION

1. Field of the Invention

The present invention relates to a cost-effective, continuously operating process for the preparation of succinic anhydride, in which only very small amounts of the γ-butyrolactone conventionally forming as a by-product in the hydrogenation of maleic anhydride are found and no monocarboxylic acids and no hydroxy-carboxylic acids of carbon numbers<4 are formed.

Succinic anhydride is an important starting product for the preparation of thermoplastic polyesters which have particular mechanical and chemical properties and good biodegradability.

2. Description of the Related Art

It is known to prepare succinic anhydride from succinic acid discontinuously by a dehydration reaction by introducing acetic anhydride vapours into molten succinic acid (GB 507 592, cited in Ullmann, Enzyklopädie der technischen Chemie, [Encyclopaedia of Industrial Chemistry], 3rd Edition (1953), Volume 4, p. 318).

It is further known to hydrogenate maleic anhydride in the batch process over Ni (U.S. Pat. No. 2,198,153), cited in Ullman, Enzyklopädie der technischen Chemie, [Encyclopaedia of Industrial Chemistry], 3rd Edition (1953), Volume 4, p. 318) or Pd, Rh, Pt/$Al_2O_3$ (JP48/7609 (1973)) to give succinic anhydride.

It is further known to hydrogenate maleic anhydride to give succinic anhydride continuously over Pd/activated carbon (SU 721 406).

The course of the reaction can be illustrated by the following reaction diagram:

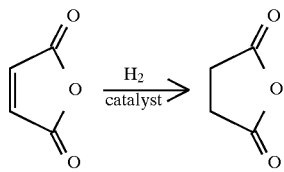

In the known processes for the preparation of succinic anhydride, predominantly discontinuous suspension methods (batch processes) are employed, in which the maleic anhydride is hydrogenated with hydrogen over pulverulent catalyst with and without solvent.

Discontinuous processes have the disadvantage that their capacity is very low relative to the reaction volume and there is thus a requirement for large reaction apparatuses and storage tanks. Energy consumption and labour requirements are relatively high.

Continuous powder catalyst processes which operate using a plurality of hydrogenation reactors connected in a cascade avoid some of these disadvantages. However, there remains the requirement of specifically metering in the pulverulent catalysts repeatedly, circulating them by pumping and filtering them off quantitatively from the reaction product. The catalyst slurry pumps are subject to high mechanical wear. Quantitative removal of the pulverulent catalysts from the reaction product is complex. In addition, there is a high risk of relatively rapidly decreasing the catalyst activity by the additional operations. It is therefore advantageous to allow the reaction to proceed over fixed catalysts. Such catalysts must have a high activity which must not decay over a relatively long period, since frequent changes of catalyst in fixed-bed reactions are likewise complex.

The hydrogenation of maleic anhydride to give succinic anhydride over Pd/activated carbon has previously been described as a continuously operating process. This catalyst has only a restricted life. Moreover, the reaction can only be carried out using a solvent.

SUMMARY OF THE INVENTION

Surprisingly, it has now been found that maleic anhydride can be hydrogenated continuously very effectively over support-free shaped bodies which are arranged in the fixed bed and are made of oxygen-free metal powders of one or more elements of the iron subgroup of subgroup VIII of the Periodic Table of the Elements (Mendeleev) to give succinic anhydride. In addition it can be useful to alloy the metals of the iron subgroup with elements of subgroup VI of the Periodic Table of the Elements having activating action. The powders used in this can additionally have low contents of non-catalytically active elements (e.g. silicon, aluminium, titanium, carbon), without the high activity being decreased. The solid bodies must have a compressive strength of 20–250N and an internal surface area of 10–90 $m^2$/g.

The invention thus relates to a process for the continuous preparation of succinic anhydride by catalytic hydrogenation of maleic anhydride, which is characterized in that the hydrogenation is carried out in the liquid phase at a $H_2$ pressure of 50–400 bar, a 10–80 times molar amount of $H_2$, based on the stoichiometric amount, and at a temperature of 60°–180° C. and on oxygen-free support-free catalysts which are arranged in the fixed bed and are present as pressed shaped bodies produced from metal powders and have a compressive strength of 20–250N and an internal surface area of 10–90 $m^2$/g and in which the metal powders contain 60–100% by weight of one or more ferrous metals, 0–15% by weight of one or more metals of subgroup VI and 0–25% by weight of one or more hydrogenation-inert elements from the group consisting of aluminium, silicon, titanium and carbon, all based on the total weight of metal powder.

DETAILED DESCRIPTION OF THE INVENTION

The compressive strength of the support-free shaped bodies can be determined as specified in DIN 50 106.

Support-free shaped bodies can be tested for the internal surface areas in accordance with the claims and thus for usability for the process according to the invention by methods which have been described by F. M. Nelsen and F. T. Eggertsen, Analyt. Chem. 30 (1958), pp. 1387–1390 and S. J. Gregg and K. S. W. Sing, Adsorption, Surface Area and Porosity, London 1982, Chapters 2 and 6.

The iron subgroup of subgroup VIII of the Periodic Table of the Elements (Mendeleev) contains the elements iron, cobalt and nickel. The support-free shaped bodies to be used according to the invention contain one or more of these metals in amounts of at least 60, preferably at least 70, in particular at least 80% by weight based on the total weight of the support-free shaped bodies.

Subgroup VI of the Periodic Table of the Elements contains the elements chromium, molybdenum, and tungsten. The support-free shaped bodies to be used according to the invention contain one or more of these metals in amounts of 0–15 % by weight. If they are present, the metal powders contain at least 0.1, preferably at least 0.3, in particular at least 0.5, % by weight, based on support-free shaped bodies; they contain one or more of these metals in amounts of at most 15, preferably at most 10 and in particular at most 5% by weight, based on support-free shaped bodies.

The support-free shaped bodies to be used according to the invention can, furthermore—in each case based on support-free shaped bodies—contain up to 25, preferably up to 15, % by weight of other elements; examples of such elements which are not catalytically active include aluminium, silicon, titanium and carbon. According to a preferred embodiment, the support-free shaped bodies contain, apart from the metals of subgroups VIII and VI, no more than 10% by weight of aluminium and no more than 5% by weight of other elements.

For the hydrogenation process, pure hydrogen precompressed to a pressure of 50–400 bar, preferably 100 to 400 bar, particularly preferably 150–300 bar, is used, where a 20 to 60 times, preferably 20 to 40 times, molar amount of hydrogen is employed, based on the stoichiometric amount.

The hydrogenation is performed continuously in the fixed-bed process on the support-free shaped bodies of the type described serving as hydrogenation catalysts by allowing the liquid maleic anhydride to be hydrogenated to flow either co-currently with the previously admixed hydrogen ascending from bottom to top over the shaped bodies packed into the hydrogenation reactor or else coming from the bottom in the opposite direction to hydrogen flowing in from the top (counter-current process). The process according to the invention can obviously also be carried out in solvents. Suitable solvents which are inert under the reaction conditions are, for example, di-n-propyl ether, di-iso-propyl ether, di-n-butyl ether, di-iso-butyl ether, tetrahydrofuran, dioxane, pyran, γ-butyrolactone. Preferably, the process according to the invention is carried out without solvent or in γ-butyrolactone as a solvent inherent to the system.

The hydrogenation process is carried out at temperatures of 60° to 180° C., preferably 80°–160° C., particularly preferably 100°–140° C. Lower temperatures require higher residence times or the abandonment of quantitative conversion. Higher temperatures lead to increased formation of γ-butyrolactone as a by-product.

The hourly catalyst loading can be 200 to 500 g of maleic anhydride/l of catalyst.

Maleic anhydride having a purity of >99% is used. However, maleic anhydride containing distillation refluxes (γ-butyrolactone) may also be used.

The hydrogenation reactor can be either an individual high-pressure tube made of steel or a steel alloy which is completely or partially filled with the support-free shaped bodies, where employment on gratings (wire baskets or the like) can also be useful, or else an encased high-pressure tube bundle whose individual tubes are completely or partially filled with shaped bodies.

The support-free shaped bodies can also be produced by conventional methods by pressing the metal powder on tableting and pelleting machines under high pressure, where to improve the adhesive strength of the metal particles, graphite can also be used in amounts of 0.5–1.5% by weight, based on the total weight of the constituents forming the catalyst, or adhesives can be used in small amounts.

The support-free shaped bodies are preferably produced in an oxygen-free atmosphere in order to avoid surface oxidations. Tabletted and pelleted shaped bodies having diameters of 3 to 7 mm are the most effective and most expedient for carrying out the reaction. The compressive strength of the shaped bodies, which according to the invention is at values of 20 to 250N, preferably 100 to 220N, is of considerable importance. Lower compressive strengths lead to disintegration of the shaped body or erosive wear, which would cause metallic contamination of the reaction product. Higher values require a disproportionate expenditure in the pressing, without further advantages being achieved. The internal surface area of the shaped bodies is further of considerable importance which according to the invention is at values of 10 to 90 $m^2/g$ and is decisive for as quantitative as possible a conversion of the starting materials.

Under the reaction conditions described, in this manner, completely unexpectedly, long catalyst lives of 15,000 hours and above may be achieved, which leads to catalyst consumptions<0.1% by weight, based on reaction product produced.

The reaction mixture leaving the hydrogenation reactor is depressurized, in which process the excess hydrogen can be collected and, after compression and supplementation of used hydrogen has been performed, can be reused. In a complete hydrogenation (99.9–100% conversion of the maleic anhydride) the reaction mixture comprises at least 97% by weight of succinic anhydride. It can contain in organic low boilers up to 3% by weight of γ-butyrolactone.

The oxygen-free and support-free fixed-bed catalysts to be used according to the invention do not, in contrast to support-containing catalysts, have a tendency to "bleed", that is do not have a tendency to transfer of catalyst constituents in ionic or colloidal form into the solution phase of the substrate, so that the substrate is not contaminated by heavy metals which usually can likewise only be removed from the substrate laboriously, for example using ion exchangers. The catalyst metals to be used can, for instance after relatively long use of the catalyst, be readily reprocessed and reused, since the heavy metals do not have to be separated from a support material in a complex manner.

The succinic anhydride produced has a content of catalyst constituents of <1 ppm, is obtained in a purity of ≧99.9% by weight after low-boiler removal by distillation and can therefore be used for further employment without any further purification, for example even for the production of polymers.

The colourless and clear succinic anhydride melt obtained after distillation can either be crystallized in crystallization apparatuses of conventional type or processed via flaking drums to give pourable flakes.

EXAMPLES

Example 1

A vertically upright, heat-insulated high-pressure tube made of stainless steel of 45 mm internal diameter and 1 m length was filled with 1.4 l of a hydrogenation catalyst produced by tableting nickel powder, which hydrogenation catalyst, at a cylinder height of 5 mm and a diameter of 5 mm, had a compressive strength of 147N on the cylinder peripheral surface and an internal surface area of 33 $m^2/g$. Through this tube, together with 20 times the molar amount of high-purity hydrogen at a pressure of 300 bar, were continuously pumped 420 g per hour of a clear maleic anhydride melt produced in a melting vessel, that is to say ascending from bottom to top.

Maleic anhydride melt and hydrogen were conducted together in advance through a heat exchanger and heated sufficiently so that they entered the high-pressure tube at a temperature of 130° C. The mixture of liquid reaction product and excess hydrogen leaving the high-pressure tube was conducted into a separator from where the hydrogen, after replacement of the amount used, was pumped again together with new maleic anhydride melt into the preheater and from there once more into the high-pressure tube.

The colourless and clear reaction product melt was examined by gas chromatography after depressurization to atmospheric pressure and cooling.

In organic low-boilers, it contained 1.5% by weight of γ-butyrolactone, so that the succinic anhydride content of the organic reaction product was 98.5% by weight.

The succinic anhydride produced was obtained in a purity of 99.9% by weight after removal of the low boiler by distillation.

The catalyst was unchanged in activity after a running time of 4100 hours, so that the composition of the reaction product did not change over this period.

Example 2

In a high-pressure tube as in Example 1, at a temperature of 125° C. and a hydrogen pressure of 200 bar, the hydrogen, in reverse reaction flow to that in Example 1, was conducted in the opposite direction to the ascending maleic anhydride melt, in which case, an amount identical to that in Example 1 was hydrogenated per hour. The catalyst had been produced by tableting a powdered nickel-iron alloy. The alloy contained a proportion of iron in the nickel of 15% by weight. The tablets, at a cylinder height of 5 mm and a diameter of 5 mm, had a compressive strength of 137N on the cylinder peripheral surface and an internal surface area of 74 $m^2/g$.

After a running time of 3200 hours, the conversion of the maleic anhydride used was 99.95% by weight. The content of γ-butyrolactone in the reaction product was 1.85% by weight, so that the succinic anhydride content of the reaction product was 98.10% by weight (remainder=0.05% by weight of unreacted maleic anhydride).

After removal of the impurities by distillation, the succinic anhydride produced was obtained in a purity of 99.9% by weight.

Example 3

A vertically upright, heat-insulated high-pressure tube made of stainless steel of 45 mm internal diameter and 1 m length was filled with 1.4 l of a hydrogenation catalyst produced by tableting powder of a Ni/Mo alloy having an Mo content of 1.75 %, which catalyst, at a cylinder height of 5 mm and a diameter of 5 mm, had a compressive strength of 191N and an internal surface area of 58 $m^2/g$. Through this tube, together with thirty times the molar amount of high-purity hydrogen under a pressure of 300 bar, were pumped 560 g of maleic anhydride melt per hour, that is ascending from bottom to top.

Maleic anhydride melt and hydrogen were brought to a temperature of 120° C. before entry into the high-pressure tube.

After a running time of 1980 hours, the conversion of the maleic anhydride used was 100% by weight. The content of γ-butyrolactone in the reaction product was 1.07% by weight, so that the succinic anhydride content was 98.93% by weight. After removal of the impurity by distillation, the succinic anhydride produced was obtained in a purity of 99.9% by weight.

Example 4

In a high-pressure tube as in Example 1, but made of high-pressure steel N 9, an identical amount per hour of maleic anhydride was hydrogenated at a temperature of 120° C. and a hydrogen pressure of 300 bar. The catalyst had been produced by tableting powder of an Ni/Mo/Al alloy having an Mo content of 1.02% by weight and an Al content of 6.1% by weight. The tablets, at a cylinder height of 5 mm and a diameter of 5 mm, had a compressive strength of 210N and an internal surface area of 71 $m^2/g$.

After a running time of 2800 hours, the content of the succinic anhydride in the reaction product was 98.9% by weight and the content of γ-butyrolactone was 1.1% by weight.

Example 5

In a high-pressure tube as in Example 1, an identical amount per hour of maleic anhydride was hydrogenated at a temperature of 125° C. and a hydrogen pressure of 300 bar. The catalyst had been produced by tableting a powdered Ni/Fe/Mo alloy. The alloy contained an Fe portion of 15% and a Mo content of 1.4 %. The tablets, at a cylinder height of 3 mm and a diameter of 3 mm, had a compressive strength of 162N and an internal surface area of 68 $m^2/g$.

After a running time of 1700 hours, the conversion of the maleic anhydride used was 99.95% by weight. The content of γ-butyrolactone in the reaction product was 1.27% by weight, so that the succinic anhydride content of the reaction product was 98.68% by weight (remainder=0.05% by weight of unreacted maleic anhydride).

Example 6

In a high-pressure tube as in Example 1, an amount of 420 g of maleic anhydride per hour was hydrogenated at a temperature of 130° C. and a hydrogen pressure of 300 bar. The catalyst had been produced by tableting a powdered Ni/Al/Si alloy having an Al content of 5.4% by weight and an Si content of 0.2% by weight.

The tablets, at a cylinder height of 3 mm and a diameter of 3 mm, had a compressive strength of 148N and an internal surface area of 61 $m^2/g$.

After a running time of 1400 hours, the conversion of the maleic anhydride used was 99.9% by weight. The content of γ-butyrolactone in the reaction product was 1.0% by weight, so that the succinic anhydride content was 98.9% by weight (remainder=0.1% by weight of unreacted maleic anhydride).

Example 7

In a high-pressure tube as in Example 1, an amount of 200 g of maleic anhydride, dissolved as a 30% strength by weight solution in γ-butyrolactone, was hydrogenated per hour at a temperature of 120° C. and a hydrogen pressure of 300 bar. The catalyst had been produced by tableting a powdered Ni/Al alloy having an Al content of 6.1% by weight.

The tablets, at a cylinder height of 3 mm and a diameter of 3 mm, had a compressive strength of 156N on the cylinder peripheral surface and an internal surface area of 69 $m^2/g$.

After a running time of 1680 hours, the conversion of the maleic anhydride used was 99.9% by weight.

After removal of the solvent by distillation and a distillation of the crude succinic anhydride carried out after this, the succinic anhydride had a purity of 99.9% by weight. The γ-butyrolactone distilled off was recycled back to the process.

What is claimed is:

1. A process for the continuous preparation of succinic anhydride by catalytic hydrogenation of maleic anhydride, wherein the hydrogenation is carried out in the liquid phase at a $H_2$ pressure of 50 to 400 bar, a 10 to 80 times molar amount of $H_2$, based on the stoichiometric amount, and at a temperature of 60° to 180° C. and on oxygen-free support-free catalysts which are arranged in the fixed bed and are present as pressed shaped bodies produced from metal powders and have a compressive strength of 20 to 250N and an internal surface area of 10 to 90 $m^2/g$ and in which the metal powders contain 60 to 100% by weight of one or more ferrous metals, 0 to 15% by weight of one or more metals of subgroup VI and 0 to 25% by weight of one or more hydrogenation-inert elements from the group consisting of aluminium, silicon, titanium and carbon, all based on the total weight of metal powder.

2. The process of claim 1, wherein the metal powders contain 70 to 100% by weight of one or more ferrous metals.

3. The process of claim 2, wherein the metal powders contain 80 to 100% by weight of one or more ferrous metals.

4. The process of claim 1, wherein the metal powders, when metals of subgroup VI are present, have a content of 0.1 to 15% by weight thereof.

5. The process of claim 4, wherein 0.3 to 10% by weight of metals of subgroup VI are present.

6. The process of claim 5, wherein 0.5 to 5% by weight of metals of subgroup VI are present.

7. The process of claim 1, wherein the metal powders, when hydrogenation-inert elements are present, have a content of 0 to 10% by weight of aluminium and of 0 to 5% by weight per element of Si, Ti and C.

8. The process of claim 7, wherein the total content of the hydrogenation-inert elements is 0 to 15% by weight.

9. The process of claim 8, wherein the total content of the hydrogen-inert elements is 0 to 10% by weight.

10. The process of claim 1, wherein the shaped bodies are those having a compressive strength of 100 to 220N.

11. The process of claim 1, wherein the shaped bodies are cylindrical or spherical and have diameters of 3 to 7 mm.

12. The process of claim 1, wherein the hydrogenation is carried out at $H_2$ pressure of 100 to 400 bar.

13. The process of claim 12, wherein the hydrogenation is carried out at a $H_2$ pressure of 150–300 bar.

14. The process of claim 1, wherein a 20 to 80 times molar amount of $H_2$ is employed.

15. The process of claim 1, wherein the maleic anhydride passes through the hydrogenation reactor ascending from bottom to top, while the hydrogen required for the hydrogenation is either pumped into the reactor together with the unsaturated ester or is conducted in the opposite direction to this, flowing from top to bottom.

* * * * *